United States Patent [19]

Hilton

[11] Patent Number: 4,463,607

[45] Date of Patent: Aug. 7, 1984

[54] APPARATUS FOR DETECTING THE CONDITION OF A SHEET

[75] Inventor: Graham H. Hilton, Lovedean, England

[73] Assignee: De La Rue Systems Limited, Portsmouth, England

[21] Appl. No.: 409,213

[22] Filed: Aug. 18, 1982

[30] Foreign Application Priority Data

Aug. 20, 1981 [GB] United Kingdom ................. 8125455

[51] Int. Cl.$^3$ .............................................. G01N 33/34

[52] U.S. Cl. ........................................ 73/587; 73/159; 73/801

[58] Field of Search ............. 73/587, 658, 159, 432 Z, 73/801

[56] References Cited

U.S. PATENT DOCUMENTS 4,365,508 12/1982 Loftus .................................. 73/159

*Primary Examiner*—James J. Gill

*Attorney, Agent, or Firm*—Sughrue, Mion, Zinn, Macpeak and Seas

[57] ABSTRACT

Apparatus is disclosed for determining the degree of stiffness of a sheet, for example a banknote, the stiffness being indicative of the condition of the banknote. The banknote (4) is drawn around a bobbin-shaped drum (1) by means of a pair of belts (2, 3) which grip a central portion of the banknote. The inner belt (2) drives or is driven by the central portion of the drum (1). The concave shape of the drum (1) imparts a curvature to the banknote in an axial plane, while the banknote is simultaneously curved in an orthogonal plane as it is wrapped around the drum. As the banknote passes around the drum it emits an audible noise which is picked up by a microphone (5). The amplitude of the microphone signal (7) is proportional to the crispness of the banknote and is indicative of the age of the banknote.

8 Claims, 13 Drawing Figures

APPARATUS FOR DETECTING THE CONDITION OF A SHEET

This invention relates to a method and apparatus for determining the condition of a sheet, and is particularly applicable to paper sheets such as banknotes and other documents.

The stiffness of such a sheet is a reliable indication of its overall condition, and apparatus according to the invention for determining the stiffness of a note or document comprises means for continuously bending the note, means for conveying the note to and from the bending means, a microphone arranged to respond to noise produced by the note while it is being bent, and means responsive to a noise signal from the microphone to indicate the degree of stiffness of the note.

The note or document is preferably given a curvature in one plane and is then stressed so as to bend continuously in an orthogonal plane. In a preferred form of apparatus, the bending means and conveying means comprise a rotating drum and means for feeding the note onto and away from the drum, and for wrapping the note around a portion of the perimeter of the drum, so as to impart a curvature to the note which continuously changes along the length of the note.

In order to give the note its said curvature in one plane, the drum preferably has a radius which varies along its axis, the bending means forcing the note to adopt the irregular shape of the drum surface, so as to increase the distortion of the note as it passes around the drum.

The drum may have a concave, bobbin-like surface, the note being distorted by curvature in both axial and radial planes of the drum as it passes around the drum.

The means for feeding the note around the drum preferably comprise an inner and an outer belt arranged one on each side of the note to grip the note, the belts having a width less than the length of the drum, and the inner belt being in driving relationship with the surface of the drum.

In order that the invention may be better understood, an embodiment of the invention will now be described with reference to the accompanying drawings, wherein.

Figure 2:
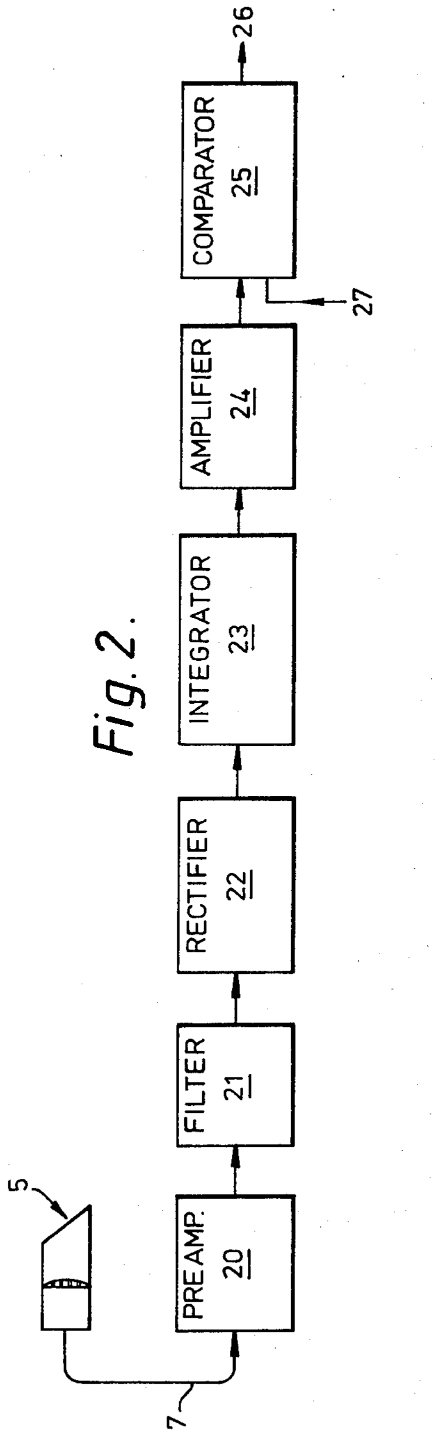
FIG. 2 is a block circuit diagram of the apparatus.
Figure 5A:
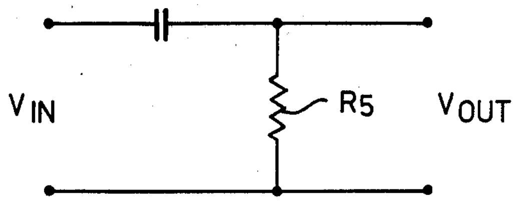
Figure 5B:
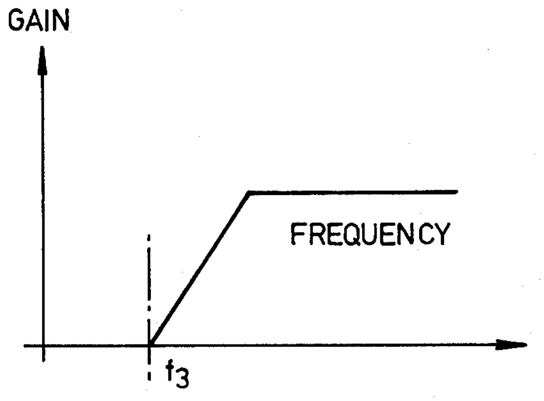

FIG. 5*a* is a circuit diagram of a high pass filter used in the embodiment of FIG. 2;

FIG. 5*b* is a graph showing frequency response of the filter of FIG. 5*a;*

Figure 6:
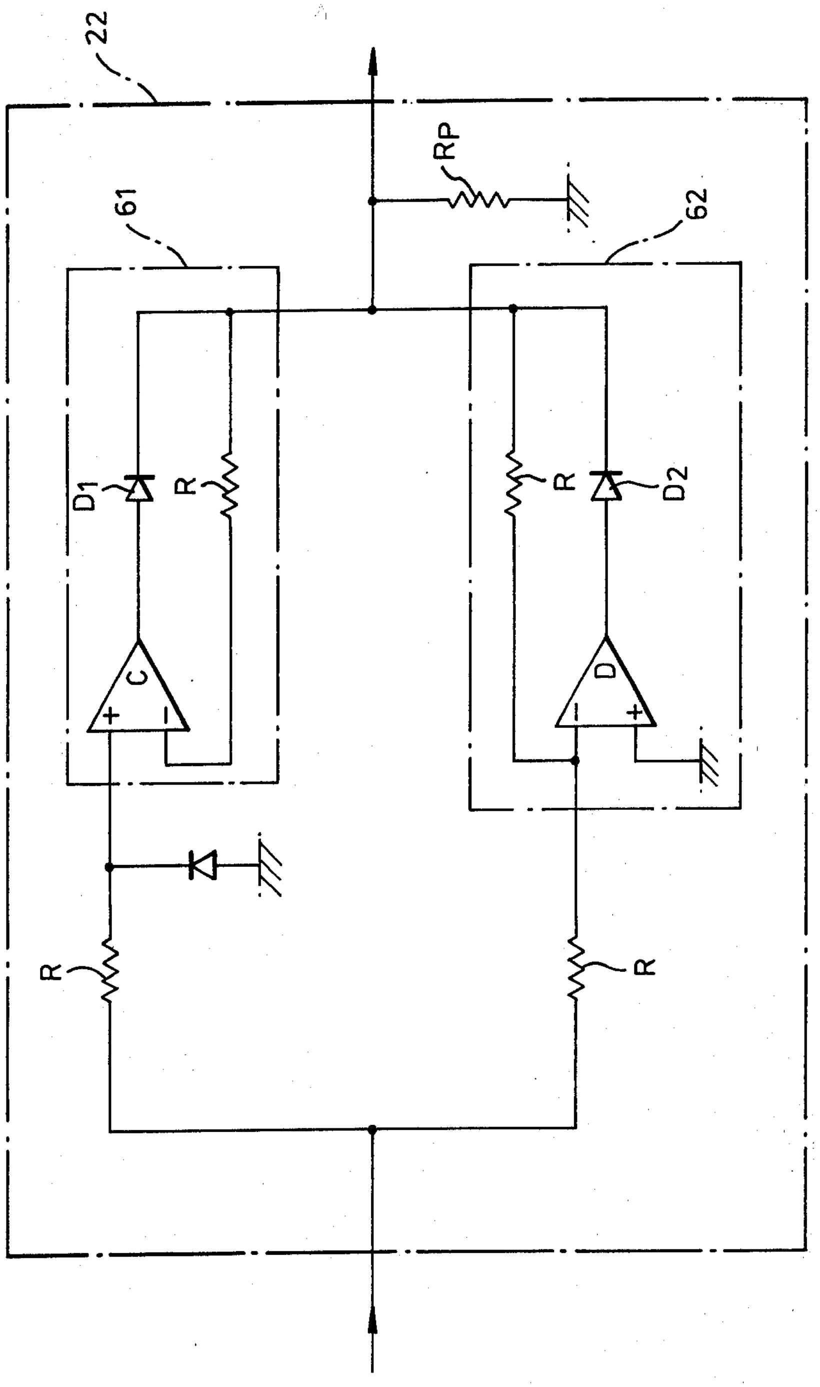
Figure 7A:
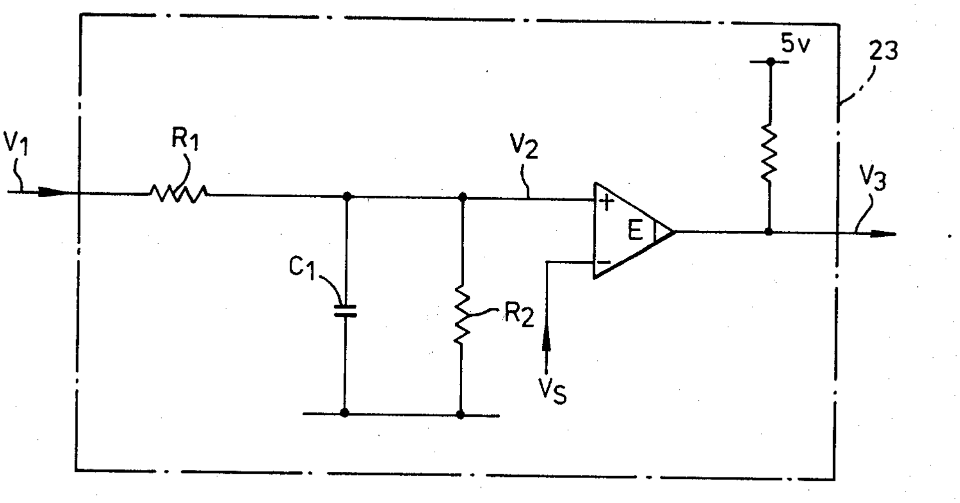
Figure 7B:
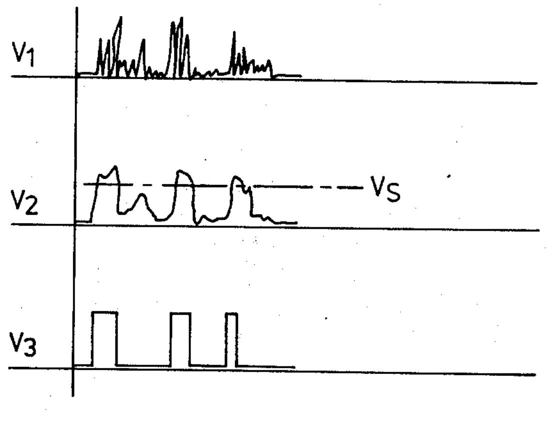

FIG. 6 is a circuit diagram of a full wave rectifier of the type used in the embodiment of FIG. 2;

FIG. 7*a* is a circuit diagram of an averaging integrator of the type used in the embodiment of FIG. 2;

FIG. 7*b* shows graphs illustrating the operation of FIG. 7*a;*

Figure 8:
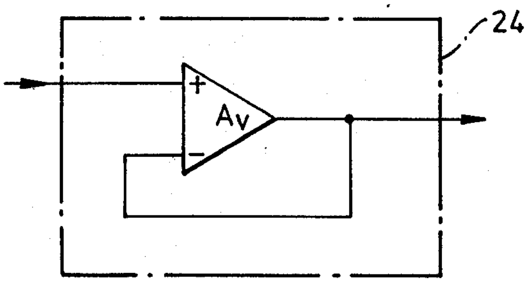
Figure 9A:
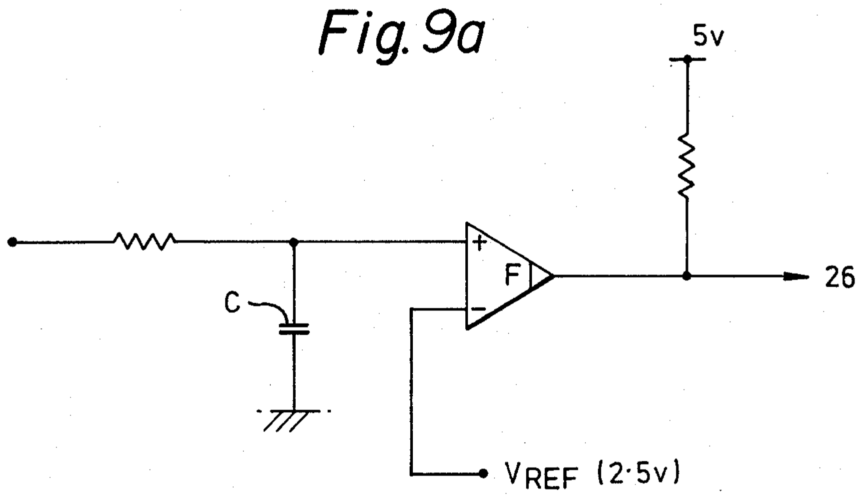
Figure 9B:
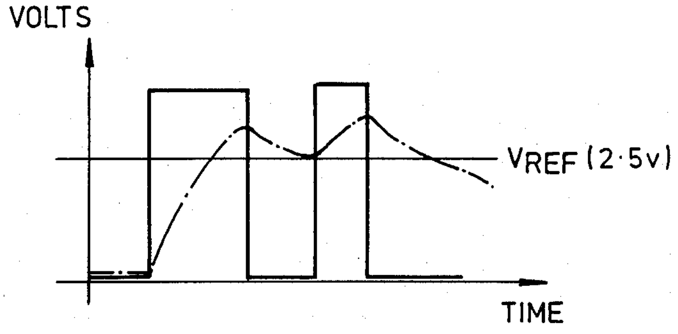

FIG. 8 is a circuit diagram of a buffer amplifier of the type used in the embodiment of FIG. 2;

FIG. 9*a* is a circuit diagram of a comparator of the type used in the embodiment of FIG. 2; and FIG. 9*b* is a graph illustrating the operation of the circuit of FIG. 9*a*.

This invention relies on the fact that sheet material such as paper produces an audible noise on being bent or distorted. The invention is particularly useful in the grading of banknotes, by sampling the level of noise produced by each banknote when passed through the same bending apparatus. It has long been known that a new banknote is much crisper than an old one, and makes a greater noise when "snapped" in the Figures. The strength of the noise produced by the banknote depends on (a) the type of paper, (b) the condition of the paper, i.e. its limpness, (c) the moisture content of the paper, and (d) the mechanical method employed to produce the noise. Assuming that factors a, c and d are constant, then the amount of noise in the apparatus should be directly proportional to (b), the condition of the paper.

Figure 1A:
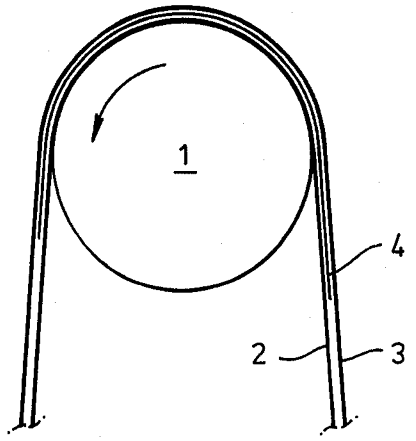
FIG. 1(*a*) is an end elevation and FIG. 1(*b*) a side elevation of the apparatus including a sheet of paper.
Figure 1B:
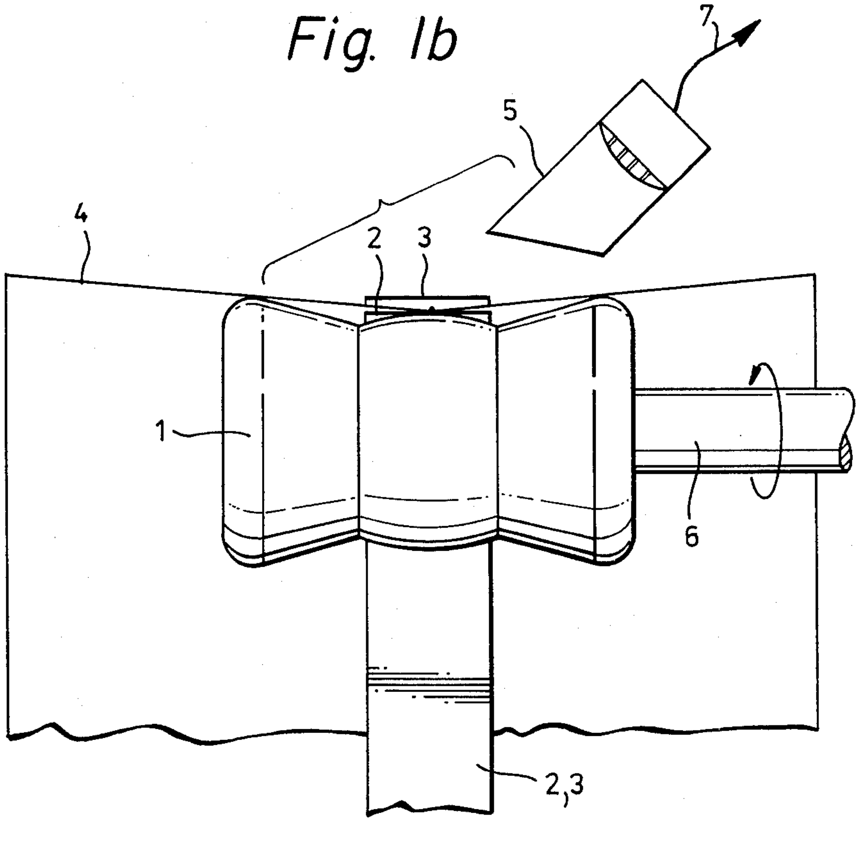

The preferred form of apparatus is shown in FIGS. 1(*a*) and 1(*b*). A sheet of paper 4 such as a banknote is conveyed between an inner belt 2 and an outer belt 3 around a bobbin-shaped roller 1 supported by an axle 6. The inner and outer belts 2, 3 are much narrower than the length of the drum 1, and the inner belt 2 is in frictional engagement with the central portion of the drum. The banknote 4 is sandwiched between the two belts. As the banknote's leading edge reaches the drum, the leading portion of the banknote is distorted from its previously flat shape. It is given a curvature in the axial plane of the drum, as shown in FIG. 1(*b*), by virtue of the concave shape of the surface of the drum. The central portion of the drum has a smaller radius than the end portions of the drum, and the belts 2, 3 force the banknote 4 to adopt the configuration of the drum surface. In addition to this curvature, the banknote is of course given a curvature in the radial plane of the drum, as shown in FIG. 1(*a*). As the banknote progresses around the surface of the rotating drum, different portions of the banknote are being bent continuously, the distortion being enhanced by the fact that the banknote is given curvatures in two orthogonal planes.

The noise produced by the distortion of the banknote is detected by a microphone 5 placed close to the drum. The amplitude of an output 7 from the microphone depends on the type and newness of the paper of the banknote.

Figure 3:
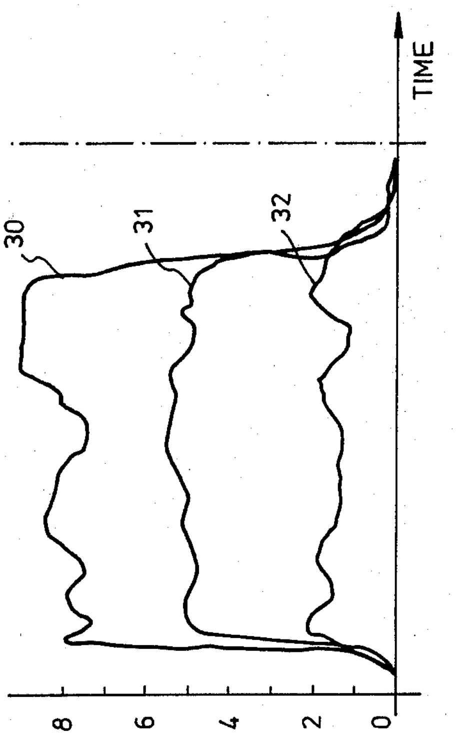
FIG. 3 is a graph of microphone voltage against time for three different types of banknote passing through the apparatus.

FIG. 2 shows a block circuit diagram for analysing the signal 7 produced by the microphone 5. The signal 7 is of the form shown in the graphs of FIG. 3, which shows voltage against time. The noisiest banknote gives a waveform 30, corresponding to a new banknote. The output waveform 31 of a normal used banknote has an intermediate level, whereas the waveform 32 of an old banknote is much lower. The waveforms of FIG. 3 are representative of "one-dollar" notes passed through the detector with their short edge leading.

In the circuit of FIG. 2, the signal 7 is analyzed within certain predetermined frequency boundaries to eliminate the ambient noise produced by the apparatus. The signal 7 is first amplified in a pre-amplifier 20, and then passed through a band pass or high pass filter 21. The A C voltage is then rectified in a full wave rectifier 22. The rectified output is integrated in an integrator 23 whose output is amplified in an amplifier 24. The amplified output is then fed into a comparator 25 in which it is compared with an adjustable threshold level 27. Threshold level 27 determines the voltage level above which a banknote is determined to be sufficiently new. The level 27 may be preadjusted by an operator. The output 26 of the comparator is a two level signal, signifying that the banknote is either fit or unfit.

Specific examples of the elements of the circuit of FIG. 2 will now be described with reference to FIGS. 4–9.

The microphone 5 is a broad band subminiature condenser microphone which exhibits a relatively flat response across most of the audible frequency range. A typical commercial microphone which is suitable for this purpose contains an internal amplifier stage which gives the microphone a high sensitivity, combined with small size, high resistance to mechanical shock and a low current drain. The diaphragm and electret of the preferred microphone is virtually unaffected by normal temperature changes and has a low sensitivity to vibration.

Figure 4:
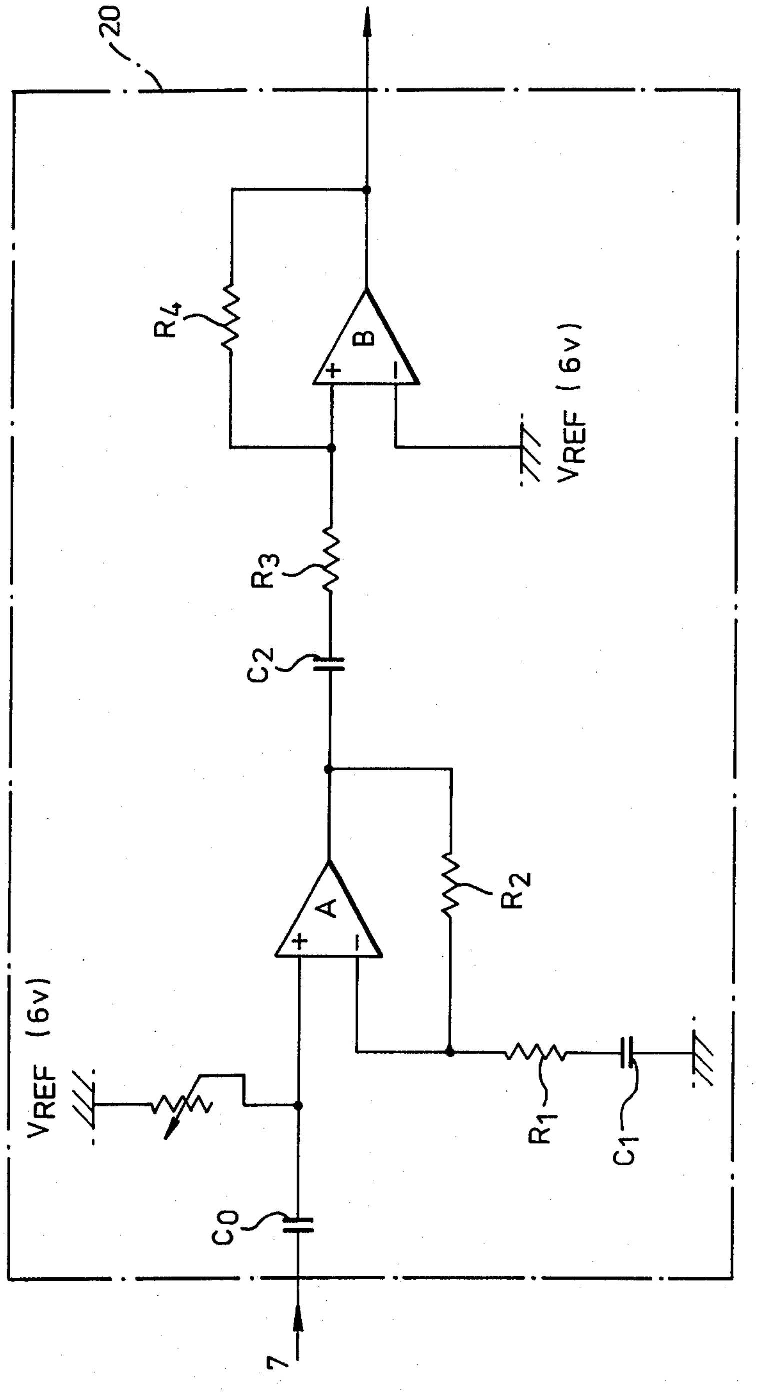
FIG. 4 is a circuit diagram of a preamplifier of the type used in the embodiment of FIG. 3.

The pre-amplifier 20 is shown in FIG. 4. The circuit consists of a two-stage single-rail pre-amplifier which is off-set to mid-rail (6 volts) to give amplification above and below 0 volts, ie. to accommodate the signal 7 from the microphone 5. The amplifiers A, B introduce high frequency poles which govern the frequency response. The maximum gain is a function of the resistances R1, R2, R3 and R4, and is approximately 44 dB. High frequency poles are introduced at 7.23 kHz, as determined by the values of capacitors C1, C2 and R1, R3.

A high pass filter 21 is shown in FIG. 5*a*, in which the input signal Vin is taken from the pre-amplifier 20. The frequency response of the filter is shown in FIG. 5*b*, where the cut off occurs at a frequency f3 equal to 7.35 kHz. The slope of the gain curve in the portion adjacent to f3 is equal to 20 dB per decade. At low frequencies, the impedance of capacitor C3 is a lot greater than that of resistor R5, so that only a small voltage drop occurs across the resistor and there is negligible signal output. At high frequencies, the impedance of the resistor R5 is much greater than that of the capacitor C3 so that a large voltage drop occurs across the resistor and Vout is approximately Vin.

A suitable full-wave rectifier 22 is shown in FIG. 6, where the input is taken from the filter of FIG. 5, and the output is transmitted to the integrator of FIG. 7. Each of the blocks 61 and 62 comprises an amplifier (C or D), a diode D1, D2 and a resistor R, and each functions as precision diode with a switch voltage given by the diode voltage drop divided by the open loop gain of the amplifier, the switch voltage being typically 6 microvolts. The blocks perform independently of each other. During positive cycles of the input voltage, diode D1 is on and diode D2 is off, the amplifier C acting as a non-inverting amplifier giving a gain of +1. During negative cycles, diode D1 is off and D2 is on, so that amplifier D acts as an inverting amplifier giving a gain of −1.

FIG. 7*a* illustrates the circuit of an averaging integrator 23. High frequency components of the input signal V1 are converted into a low frequency wave form V2 by the resistor-capacitor network R1, R2, C1, of which the charging time constant is C1R1 and the discharging time constant is R2C1. As shown in FIG. 7*b*, the input wave form V1 is averaged to produce the wave form V2. The averaged wave form V2 is compared in a comparator E with a variable voltage level Vs set by an operator at a keyboard, the variable voltage acting as a threshold for determining the condition of sorting the sheets. The output of the integrator V3, also shown in FIG. 7*b*, consists of rectangular pulses for those times where the signal V2 exeeds the voltage threshold Vs.

The rectangular output signal V3 of FIG. 7 is fed to a buffer amplifier 24, illustrated in FIG. 8. The buffer amplifier consists of an operational amplifier Av with negative feedback.

The output of the amplifier 24 is fed to a postdetection time threshold unit, illustrated in FIG. 9*a*, which corresponds to the comparator 25 of FIG. 2. The postdetection time threshold circuit integrates the input signal in a capacitor C, resulting in the dotted wave form of FIG. 9*b*. By comparing this integrated wave form in comparator F with a predetermined reference voltage Vref, the circuit detects the duration for which the signal V2 of FIG. 7 was above the voltage threshold sort level Vs. This duration is a direct indication of the overall condition of a sheet, the value of the predetermined reference voltage Vref (2.5 volts) being equivalent to the minimum duration that is acceptable, in the minimum overall condition. If this minimum condition is not met, the sheet could be sorted to a reject outlet. The output signal 26 of the circuit is a digital signal which is either "one" or "zero", in accordance with the result of the comparison.

This stage is used in order to remove any inherent spikes in the wave-form that might arise due to the presence of glue and tape or due to a high degree of limpness caused by continuous folding. The maximum time constant that can be allowed is governed by the duration between the passage of consecutive sheets through the apparatus, which is typically 30 milliseconds.

There are clearly many variations on the types of circuit elements which could be employed for analyzing the output signal of the microphone 5. It would be possible, for example, to use more than one threshold level for the comparison effected in the circuit of FIG. 7*a*. The apparatus may include sorting apparatus for diverting a bank note depending on its condition, for example.

1. Apparatus for determining the stiffness of a note or document comprising means (1, 2) for conveying the note (4) along a flow path, bending means (3) at a given location in the flow path for continuously bending the note (4) during its movement past that location, a microphone (5) arranged to respond to noise produced by the note while it is being bent, and means (20–25) responsive to a noise signal from the microphone to indicate the degree of stiffness of the note.

2. Apparatus in accordance with claim 1, wherein the bending means gives the note a curvature in a first plane and then stresses the note so as to bend it continuously in a second plane orthogonal to the first plane.

3. Apparatus in accordance with claim 1 or 2, wherein the bending means comprise a rotating drum (1), the conveying means (2, 3) feeding the note onto and away from the drum and wrapping the note around a portion of the perimeter of the drum, so as to impart a curvature to the note which continuously changes along the length of the note.

4. Apparatus in accordance with claim 3, wherein the drum has a radius which varies along its axis, the bending means forcing the note to adopt the irregular shape of the drum surface and so giving it a curvature in the first plane, so as to increase the distortion of the note as it passes around the drum.

5. Apparatus in accordance with claim 4, wherein the drum has a concave, bobbin-like shape, the note being distorted by curvature in both axial and radial planes of the drum as the note passes around the drum.

6. Apparatus in accordance with claim 3, wherein the means for feeding the note onto, around and away from the drum comprise an inner (2) and an outer (3) belt arranged one on each side of the note to grip the note, the belts having a width less than the length of the drum.

7. Apparatus in accordance with claim 6, wherein the said inner belt is in frictional driving relationship with a central portion of the surface of the drum.

8. Apparatus in accordance with claim 1, wherein the means responsive to the noise signal from the microphone integrates (23) the noise signal, and compares the integrated value with a predetermined threshold value, the result of the comparison being used to provide a signal (26) indicative of the degree of stiffness of the note.

* * * * *